US00PP29739P3

(12) United States Plant Patent
Klemm et al.

(10) Patent No.: US PP29,739 P3
(45) Date of Patent: Oct. 9, 2018

(54) POINSETTIA PLANT NAMED 'NPCW16260'

(50) Latin Name: *Euphorbia pulcherrima*
Varietal Denomination: NPCW16260

(71) Applicant: Klemm+Sohn GmbH & Co. KG, Stuttgart (DE)

(72) Inventors: Nils Klemm, Stuttgart (DE); Guido von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 15/530,710

(22) Filed: Feb. 17, 2017

(65) Prior Publication Data

US 2018/0242495 P1 Aug. 23, 2018

(51) Int. Cl.
*A01H 5/12* (2018.01)
*A01H 6/38* (2018.01)

(52) U.S. Cl.
USPC ..... Plt./303
CPC ..... *A01H 6/385* (2018.05)

(58) Field of Classification Search
USPC ..... Plt./303, 304, 306
See application file for complete search history.

(56) References Cited

PUBLICATIONS

"Selecta Catalog," 2016—(10 pages total)(obtained from the Internet on Mar. 24, 2018).*

* cited by examiner

*Primary Examiner* — Susan McCormick Ewoldt
(74) *Attorney, Agent, or Firm* — Barbara Campbell; Cochran Freund & Young LLC

(57) ABSTRACT

A new poinsettia plant particularly distinguished by having broad marbled cream and dark pink bracts, a triangular plant form, an upright growth habit, and excellent keeping quality, is disclosed.

1 Drawing Sheet

Genus and species: *Euphorbia pulcherrima.*
Variety denomination: 'NPCW16260'.

BACKGROUND OF THE NEW PLANT

The present invention comprises a new and distinct variety of poinsettia, botanically known as *Euphorbia pulcherrima* and hereinafter referred to by the variety name 'NPCW16260'. 'NPCW16260' was discovered in November 2013 from an induced mutation of the irradiation of the parent variety 'NPCW11203' (unpatented).

In April 2014, 'NPCW16260' was first asexually propagated by apical vegetative cuttings. 'NPCW16260' was found to reproduce true to type in successive generations of asexual propagation via apical vegetative cuttings in Stuttgart, Germany.

SUMMARY

The following are the most outstanding and distinguishing characteristics of this new variety when grown under normal horticultural practices in Stuttgart, Germany.

1. Broad marbled cream and dark pink bracts;
2. A triangular plant form;
3. An upright growth habit; and
4. Excellent keeping quality.

DESCRIPTION OF THE PHOTOGRAPH

This new poinsettia plant is illustrated by the accompanying photograph which shows an overall view of the plant. The photograph is of a plant approximately 16 to 18-weeks-old grown indoors in Stuttgart, Germany in December 2016.

The colors shown are as true as can be reasonably obtained by conventional photographic procedures.

DESCRIPTION OF THE NEW VARIETY

The following detailed descriptions set forth the distinctive characteristics of 'NPCW16260'. The data which define these characteristics were collected from asexual reproductions carried out in Stuttgart, Germany. Data was collected on nineteen-week-old plants (after potting) grown indoors in Stuttgart, Germany under greenhouse conditions in December 2016. Color references are to The R.H.S. Colour Chart of The Royal Horticultural Society of London (R.H.S.), 5$^{th}$ edition (2007).

Classification:
- *Family.*—Euphorbiaceae.
- *Species.*—*Euphorbia pulcherrima.*
- *Common name.*—Poinsettia.
- *Variety.*—'NPCW16260'.

Parentage: Mutation from the poinsettia variety 'NPCW11203'.

Growth:
- *Time to produce a rooted cutting.*—4 weeks.
- *Blooming habit.*—Intermittent.
- *Flowering response time.*—Approximately 58 days.
- *Keeping quality.*—Good.

Plant description:
- *Form.*—Triangular.
- *Growth habit.*—Upright.
- *Height.*—23.0 cm to 26.0 cm.
- *Width.*—25.0 cm to 30.0 cm.
- *Number of branches.*—5 to 6.
- *Average number of inflorescences per plant.*—5 to 6.
- *Disease and pest resistance.*—None observed.

Propagation:
*Type cuttings.*—Apical cuttings.
*Time to produce a rooted cutting.*—4 weeks.
*Rooting habit and root color.*—Freely branching root habit and color of young roots is RHS 155D.

Lateral branches:
*Color.*—RHS 143C.
*Length.*—21.0 cm to 23.0 cm.
*Internode length.*—1.0 cm to 2.5 cm.
*Diameter.*—0.5 cm to 0.7 cm.
*Branching habit.*—Freely branching.
*Number of lateral branches per plant.*—5 to 6.
*Texture.*—Smooth.

Leaves:
*Quantity.*—6 to 7 per lateral branch.
*Arrangement.*—Alternate.
*Number of lobes on the leaf blade.*—1 to 3.
*Lobation depth.*—Shallow.
*Depth of the deepest sinus of the leaf blade.*—Approximately 0.5 cm.
*Shape.*—Ovate.
*Apex.*—Acute.
*Base.*—Obtuse.
*Margin.*—Serrate.
*Length.*—6.0 cm to 9.0 cm.
*Width.*—5.0 cm to 7.0 cm.
*Texture (both surfaces).*—Smooth on the upper surface but the lower surface is slightly pubescent.
*Vein color.*—Upper surface: Transparent. Lower surface: RHS 139C.
*Variegation.*—Absent.
*Venation pattern.*—Reticulate.
*Color.*—Mature foliage: Upper surface: Darker than RHS 139A. Lower surface: RHS N138B. Immature foliage: Upper surface: RHS 141A. Lower surface: RHS 139B.
*Leaf petiole.*—Length: 2.5 cm to 5.0 cm. Diameter: 0.2 cm to 0.3 cm. Color (both upper and lower surfaces): RHS 183A. Texture: Smooth. Strength: Medium.

Inflorescence:
*Lastingness of inflorescence on the plant.*—4 weeks.
*Natural flowering season.*—End of November.
*Diameter.*—18.0 cm to 22.0 cm.
*Height.*—2.0 cm to 4.0 cm.
*Fragrance.*—Absent.

Bracts:
*Number of bracts per inflorescence.*—6 to 9.
*Shape.*—Ovate.
*Apex.*—Acute.
*Base.*—Obtuse.
*Margin.*—Serrate.
*Size.*—Length: 8.0 cm to 11.0 cm. Width: 4.0 cm to 6.0 cm.
*Texture (both upper and lower surfaces).*—Smooth.
*Venation pattern.*—Reticulate.
*Vein color.*—Upper surface: RHS 19C. Lower surface: RHS 19C (middle vein is slightly reddish).
*Bract color (both upper and lower surfaces).*—Marbled RHS 19C and RHS 63A.
*Bract petiole.*—Length: 0.5 cm to 2.0 cm. Diameter: 0.2 cm to 0.3 cm. Color: Upper (part) surface: RHS 19C. Lower (part) surface: Close to RHS 180C. Texture: Smooth. Strength: Medium.

Cyme:
*Diameter.*—1.0 cm to 2.0 cm.
*Cyathia number.*—5 to 7 per inflorescence.
*Deformation of glands of the cyathium.*—Absent.
*Timing of opening of cyanthia.*—End of November (first pollen and nectar cups); stigmas appear 1 to 2 weeks later.

Cyanthium:
*Shape.*—Ovate.
*Diameter.*—About 0.3 cm.
*Length.*—0.4 cm.
*Color.*—RHS 144A and RHS 144B.

Peduncle:
*Color.*—RHS 144B.
*Length.*—0.2 cm to 0.25 cm.
*Diameter.*—0.1 cm.
*Texture.*—Smooth.
*Strength.*—Weak to medium.

Nectar cups:
*Number.*—1 per cyathium.
*Diameter.*—0.1 cm.
*Length.*—0.3 cm.
*Color.*—RHS 3A.

Reproductive organs:
*Stamen number.*—5 to 10.
*Stamen shape.*—Ovate.
*Filament length.*—0.25 cm.
*Filament color.*—RHS 149 D.
*Pollen quantity.*—Sparse.
*Pollen color.*—RHS 4D.
*Gynoecium.*—Pistil quantity per cyathium: 1. Pistil length: 0.25 cm. Stigma form: Divided in 3 parts. Stigma color: RHS 36D. Style length: 0.1 cm. Style color: RHS 144B. Ovary length: 0.2 cm. Ovary color: RHS 144A.

Fruit and seed set: Absent.

COMPARISON WITH PARENTAL LINE AND KNOWN VARIETY

'NPCW16260' is distinguished from its parent 'NPCW11203' as described in Table 1.

TABLE 1

| Characteristic | Variety 'NPCW16260' | Parent 'NPCW11203' |
|---|---|---|
| Bract color | Marbled cream and dark pink | Red-pink |

'NPCW16260' can be compared to the commercial Poinsettia plant variety 'NPCW10184' (U.S. Plant Pat. No. 22,847). Differences between the two varieties are described in Table 2.

TABLE 2

| Comparison with Similar Variety | | |
|---|---|---|
| Characteristic | 'NPCW16260' | Commercial line 'NPCW10184' |
| Bract shape | Broader than 'NPCW10184' | Elongated |
| Plant shape | Wider than 'NPCW10184' | Slimmer than 'NPCW16260' |
| Bract color | Strong marbled pattern | Weaker marbled pattern than 'NPCW16260' |

We claim:

1. A new and distinct variety of poinsettia plant named 'NPCW16260' as illustrated and described herein.

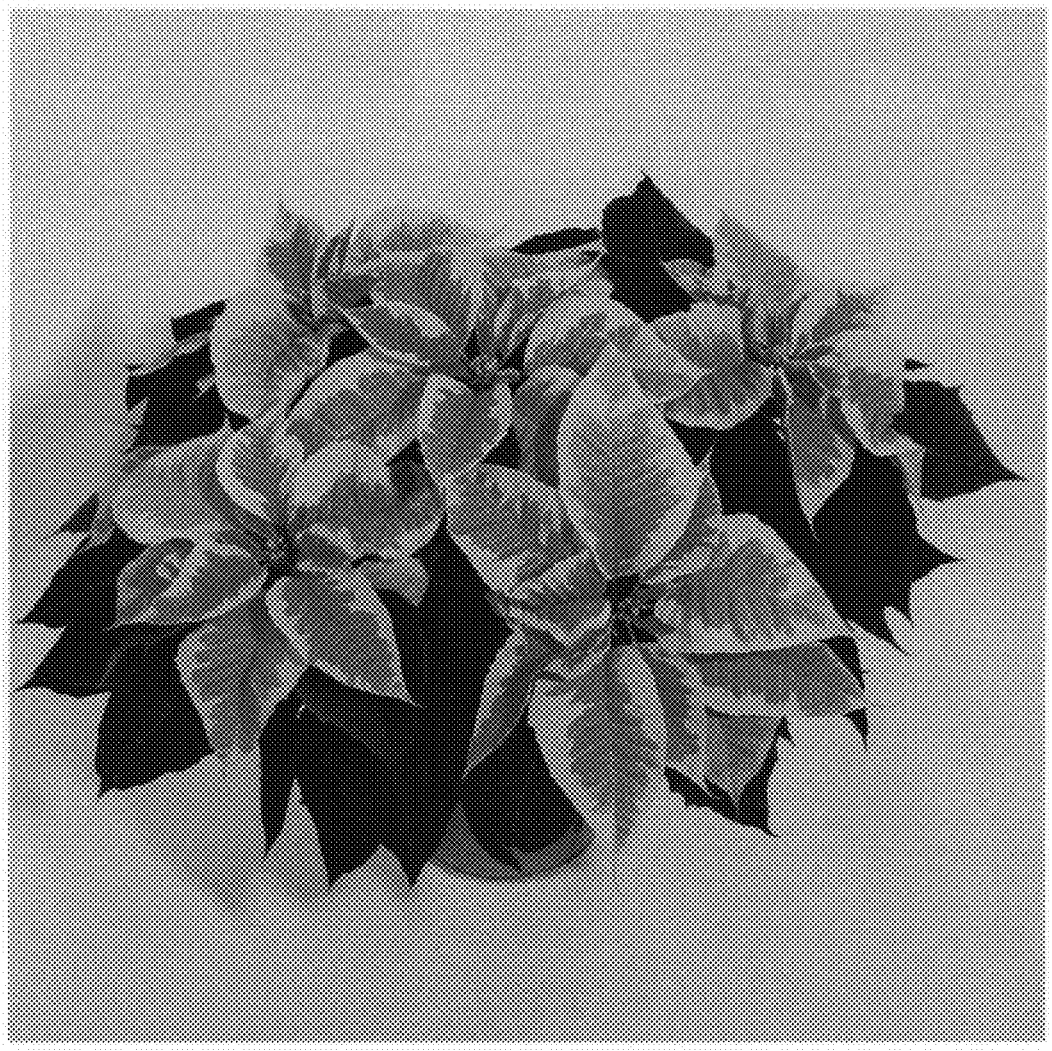

* * * * *